US008642747B2

(12) United States Patent
Sharma et al.

(10) Patent No.: US 8,642,747 B2
(45) Date of Patent: *Feb. 4, 2014

(54) GENETIC MODIFICATION OF TARGETED REGIONS OF THE CARDIAC CONDUCTION SYSTEM

(75) Inventors: Vinod Sharma, Blaine, MN (US); Walter H. Olson, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 65 days.

This patent is subject to a terminal disclaimer.

(21) Appl. No.: 13/224,593

(22) Filed: Sep. 2, 2011

(65) Prior Publication Data

US 2012/0065253 A1    Mar. 15, 2012

Related U.S. Application Data

(63) Continuation of application No. 10/423,595, filed on Apr. 25, 2003, now Pat. No. 8,013,133.

(51) Int. Cl.
*A61K 48/00* (2006.01)
*C12N 15/00* (2006.01)
*C07H 21/02* (2006.01)

(52) U.S. Cl.
USPC .............. 536/23.1; 435/320.1; 514/44 R

(58) Field of Classification Search
USPC ............... 435/320.1; 514/44 R; 536/23.1
See application file for complete search history.

(56) References Cited

U.S. PATENT DOCUMENTS

| | | | |
|---|---|---|---|
| 4,881,979 A | 11/1989 | Lewis | |
| 5,487,753 A | 1/1996 | MacCarter | |
| 5,817,136 A | 10/1998 | Nappholz | |
| 6,188,926 B1 | 2/2001 | Vock | |
| 6,214,620 B1 | 4/2001 | Johns | |
| 6,323,026 B1 | 11/2001 | Keating | |
| 6,376,471 B1 | 4/2002 | Lawrence | |
| 8,013,133 B2 * | 9/2011 | Sharma et al. ............ | 536/23.1 |
| 2002/0022259 A1 | 2/2002 | Lee | |
| 2002/0155101 A1 | 10/2002 | Donahue | |

FOREIGN PATENT DOCUMENTS

| | | |
|---|---|---|
| WO | WO 97/23598 | 7/1997 |
| WO | WO 98/02040 | 1/1998 |
| WO | WO 98/02150 | 1/1998 |
| WO | WO 02/33111 | 4/2002 |
| WO | WO 02/087419 | 11/2002 |
| WO | WO 02/098286 | 12/2002 |

OTHER PUBLICATIONS

2008, Perez et al., Europace, pp. 161-163.*
2006, Israel CW., Europace, vol. 8, pp. 89-95.*
European Search Report for Appln. No. EP08013466.1 dated Dec. 18, 2009; pp. 4.
Office Action mailed Nov. 10, 2010 for U.S. Appln. No. 12/102,550; 50 pgs.
Baroudi et al., "Novel Mechanism for Brugada Syndrome," Circ. Res. vol. 88, p. 16 (Jun. 22, 2001).
Benson, D.A. et al., "GenBank", Nucl. Acids Res., vol. 25, p. 10-16 (1997).
Caplen, N., "Nucleic Acid Transfer Using Cationic Lipids," Methods in Molecular Biology, vol. 133, Gene Targeting Protocols, Kmeic $2^{nd}$ ed., p. 1-35 (2002).
Clark et al., "Cell Ines for the Production of Recombinant Adeno-Associated Virus," Human Gene Ther., vol. 6, p. 1329-1341, (1995).
Felgner, P., "Cationic Liposome-Mediated Transfection with Lipofectin Reagent," Methods in Molecular Biology, vol. 7, Gene Transfer and Expression Protocols, p. 81-89 (1991).
Graham, F. et al., "Manipulation of Adenovirus Vectors," Methods in Molecular Biology, vol. 7, Gene Transfer and Expression Protocols, p. 109-206 (1991).
Guzman, R.J. et al., "Efficient Gene Transfer into Myocardium by Direct Injection of Adenovirus Vectors," Cir. Res., vol. 73, No. 6, p. 1202-1207 (Dec. 1993).
Haisma et al., "Targeting of Adenoviral Vectors Through a Bispecific Single Chain Antibody", Cancer Gene Ther., vol. 7, No. 6, p. 901-904 (2000).
Han et al., "Ligand-Directed Retroviral Targeting of Human Breast Cancer Cells," Natl. Acad. Sci., vol. 92, p. 9747-9751 (1995).
Heise, C.E., et al." Characterization of the Human Cysteine Leukotriene 2 Receptor," J. Biol. Chem, vol. 275, No. 39, p. 30531-30536 (2000).
Jiang et al., "Cell-Type Specific Gene Transfer into Human Cells with Retroviral Vectors that Display Single-Chain Antibodies", J. Virol., vol. 72, No. 12, pp. 22-70 (1993).
LaPointe et al., "Left Ventricular Targeting of Reporter Gene Expression in Vivo by Human BNP Promter in an Adenoviral Vector", Am. J. Physiol., vol. 283, p. H1439-45 (2002).
Miake, J. et al., "Biological Pacemaker Created by Gene Transfer," Nature, vol. 419, p. 132-3 (2002).
Nerbonne, J., "Molecular Basis of Functional Voltage-Gated K+ Channel Diversity in the Mammalian Myocardium", J. Physiol. vol. 525, No. 2, p. 285-98 (2000).
Omori et al., "Role of Connexin (gap junction) Genes in Cell Growth Control: Approach with Site-Directed Mutagenesis and Dominant-Negative Effects," Tox. Lett, VO1. 96, 97, p. 105-110 (Aug. 1998).
Schram, G. et al., "Differential Distribution of Cardiac Ion Channel Expression as a Basis for Regional Specialization in Electrical Function," Circ. Res. vol. 90, p. 939-50 (May 17, 2002).
Schnepp et al., "Highly Purified Recombinant Adeno-Associated Virus Vectors," Gene Therapy Protocol, $2^{nd}$, ed, p. 427-443 (2002).
Vasquez et al., "Triplex-Directed Site-Specific Genome Modification", Gene Targeting Protocols, p. 183-200 (2000).
Watkins et al., "The Adenobody Approach to Viral Targeting: Specified and Enhanced Adenoviral Gene Delivery", Gene. Ther., vol. 4, p. 1004-1012 (1997).
Bohn, Georg et al., "Express T and L Type Calcium Channel mRNA in Murine Sinoatrial Node," FEBS Letters, vol. 481, No. 1, p. 73-76 (Sep. 8, 2000).

(Continued)

*Primary Examiner* — Anoop Singh
*Assistant Examiner* — David A Montanari
(74) *Attorney, Agent, or Firm* — Mueting Raasch & Gebhardt PA

(57) ABSTRACT

Disclosed are methods and systems for preventing or treating cardiac dysfunction, particularly cardiac pacing dysfunction by genetic modification of the conduction system of the heart. In one embodiment, the invention provides a method of genetically modifying the cells by delivering to the cells one or more coding sequence in a genetic construct capable of modifying the expression of ion channels of the cells.

6 Claims, 7 Drawing Sheets

(56) References Cited

OTHER PUBLICATIONS

Cribbs, Leanne L. et al., "Cloning and Characterization of a1H from Human Heart, a Member of the T-type Ca2+ Channel Gene Family," Circ. Research, vol. 83, No. 1, p. 103-109 (Jul. 13, 1998).

Katz, A.M., "T-Type Calcium Channels May Provide a Unique Target for Cardiovascular Therapy," The European Heart Journal, vol. 1, No. Suppl. H, p. H18-H23 (Jun. 1999).

Glenn et al., Journal of Cardiovascular Nursing. American Heart Association's Top 10 Research Advances in 2002. 18(5):330-336, Nov./Dec. 2003.

Qu et al., Expression and Function of Biological Pacemaker in Canine Heart. Circulation 107:1106-1109, 2003.

Atlee et al., Cardiac Rhythm Management Devices (Part I), *Anesthesiology*, 2001; 95-1265-80.

Jeffrey et al., "Cardiac Pacing, 1960-1985, A Quarter Century of Medical and Industrial Innovation", *Circulation*, 1998; 97:1978-1991.

Lau et al., "Pacing Technology: Advances in Pacing Theshold Management", *J. Zheijang Univ-Sci B (Biomed & Biotechnol)*, 2010 11(8):634-638.

Pacemaker and ICD Developments Fact Sheet, St. Jude Medical.

Schuchert et al., "Autocapture Compatibility in Patients with the MembraneEX Lead and Affinity Pulse Generators", *Europace*, 2001, 3, 332-335.

Zaroff et al., "An Implantable Demand Pacemaker", *The Annals of Thoracic Surgery*, 1967; 4:463-467.

* cited by examiner

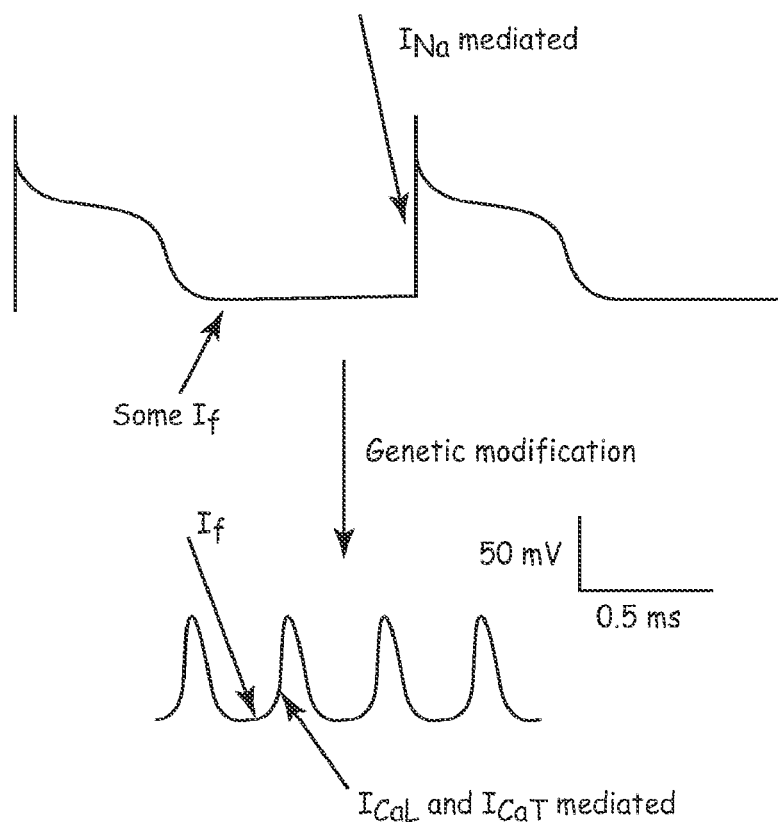

GENETIC MODIFICATION OF TARGETED REGIONS OF THE CARDIAC CONDUCTION SYSTEM

FIELD OF THE INVENTION

The present invention relates to compositions, apparatus, and methods for providing curative therapy for cardiac dysfunction, and more particularly to biological systems and methods relating to implementing curative therapeutic agents and systems for arrhythmias and cardiac pacing dysfunction.

BACKGROUND

In a normal, healthy heart, cardiac contraction is initiated by the spontaneous excitation of the sinoatrial ("SA") node, located in the right atrium. The electrical impulse generated by the SA node travels to the atrioventricular ("AV") node where it is transmitted to the bundle of His and Purkinje network, which branches in many directions to facilitate simultaneous contraction of the left and right ventricles.

In certain disease states, the heart's ability to pace properly is compromised. Currently, such dysfunction is commonly treated by the implantation of implantable pacemakers. While improving the lives of many patients, implantable pacemakers have a limited lifetime and hence, may expose a patient to multiple surgeries to replace the implantable pacemaker. Moreover, implantable pacemakers may not be capable of directly responding to the body's endogenous signaling that acts on the SA node to increase or decrease its pacing rate.

Recently, biological methods of influencing the pacing rate of cardiac cells have been developed, including the use of various drugs and pharmaceutical compositions. Developments in genetic engineering have resulted in methods for genetically modifying cardiac cells to influence their intrinsic pacing rate. For example, U.S. Pat. No. 6,214,620 describes a method for suppressing excitability of ventricular cells by overexpressing (e.g. $K^+$ channels) or underexpressing certain ion channels (e.g. $Na^+$ and $Ca^{2+}$ channels). PCT Publication No. WO 02/087419 describes methods and systems for modulating electrical behavior of cardiac cells by genetic modification of inwardly rectifying $K^+$ channels ($I_{K1}$) in quiescent ventricular cells. PCT Publication No. WO 02/098286 describes methods for regulating pacemaker function of cardiac cells with HCN molecules (HCN 1, 2, or 4 isoforms of the pacemaker current $I_f$).

A need remains, however, to implement a system of genetic modification therapy (biopacing) in cooperation with an implantable medical device (IMD) to insure successful curative therapy for cardiac dysfunction.

SUMMARY OF THE INVENTION

The present invention provides a biological pacemaker ("bio-pacemaker") that is capable of responding to physiological signals as well as facilitating and restoring synchronous contractions of the ventricles to thus mimic the function of a healthy heart. The bio-pacemaker is generated through the genetic modification of myocardial cells in a targeted region of the cardiac conduction system via delivery of a bio-pacemaker composition to the cells.

In one aspect of the invention, the bio-pacemaker composition including two or more coding sequences that encode one or more molecules is delivered to myocardial cells of the cardiac conduction system to generate a bio-pacemaker of the invention. Desirably, cells of the conduction system are genetically modified to increase their pacing rate to a level resembling the intrinsic pacing rate of the SA nodal cells in a normal heart. The bio-pacemaker composition desirably includes polynucleotides, molecules, or modified cells containing the coding sequences of the invention and is delivered to the cells, via catheters, direct injection, or equivalent delivery means.

The bio-pacemaker composition of the invention may be useful in a method of treating or preventing cardiac pacing dysfunction. Desirably, a bio-pacemaker composition of the invention is delivered to myocardial cells of the Purkinje fibers and a bio-pacemaker is generated in the cells having one or more of the following modified characteristics: 1) increased inward $Ca^{2+}$ current, 2) decreased $Na^+$ current; or 3) increased outward $K^+$ current.

In one embodiment, the bio-pacemaker of the invention is used in combination with an implantable pacemaker. Specifically, the implantable pacemaker is programmed to work in cooperation with the genetically engineered bio-pacemaker to prevent cardiac dysfunction or to sense the pacemaking action of the genetically engineered bio-pacemaker. Further, the implantable pacemaker operates to pace the heart when the pacemaking action of the bio-pacemaker is not as expected. For example, two possible triggers for resorting to the implantable pacemaker are 1) a bio-pacemaker pacing rate less than a certain predetermined threshold value and 2) an intermittent but presumably normal function of the bio-pacemaker. In case the bio-pacemaker location is the AV node, the top portions of the SA node may be ablated to isolate the atria from the AV node. When the bio-pacemaker is located in the Purkinje network, the entire AV node may be ablated.

BRIEF DESCRIPTION OF THE DRAWINGS

FIGS. 4A and 4B show the action potential (AP) characteristics of the Purkinje fiber cells before and after genetic modification in accordance with a method of this invention.

DETAILED DESCRIPTION OF THE PREFERRED EMBODIMENTS

The current invention relates to biological methods of increasing the intrinsic pacemaking rate of cells of the cardiac conduction system, such as the Purkinje fibers of the heart by genetic modification.

Figure 1:
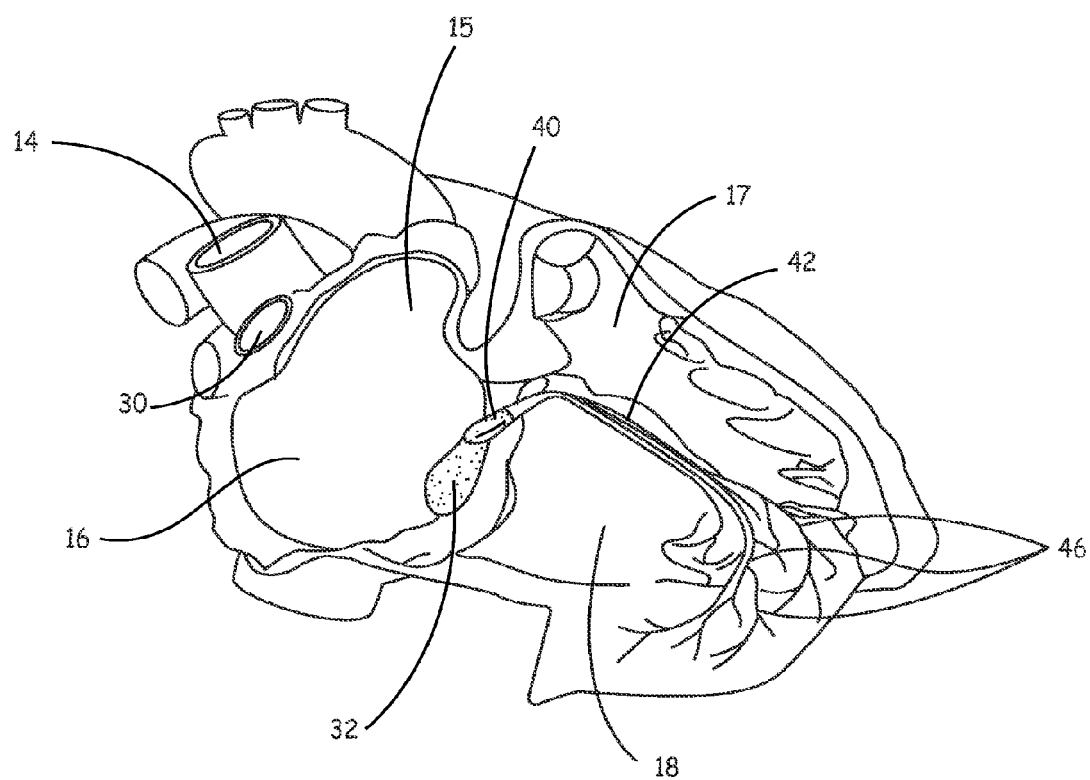
FIG. 1 is a diagram of a human heart.

FIG. 1 is a schematic diagram of a right side of a heart having an anterior-lateral wall peeled back to present a portion of a heart's intrinsic conduction system and chambers of a right atrium 16 and a right ventricle ("RV") 18. Pertinent elements of the heart's intrinsic conduction system, illustrated, in FIG. 1, include a SA node 30, an AV node 32, a bundle of His 40, a right bundle branch 42, and Purkinje fibers 46. SA node 30 is shown at a junction between a superior vena cava 14 and right atrium ("RA") 16. An electrical impulse initiated at SA node 30 travels rapidly through RA 16 and a left atrium (hot shown) to AV node 32. At AV node 32, the impulse slows to create a delay before passing on through a bundle of His 40, which branches, in an interventricular septum 17, into a right bundle branch 42 and a left bundle branch (not shown) and then, apically, into Purkinje fibers 46. Following the delay, the impulse travels rapidly throughout RV 18 and a left ventricle (not shown). Flow of the electrical impulse described herein creates an orderly sequence of atrial and ventricular contraction and relation to efficiently pump blood through the heart. When a portion of the heart's intrinsic conduction system becomes dysfunctional, efficient pumping is compromised.

Typically, a patient, whose SA node 30 has become dysfunctional, may have an implantable pacemaker system implanted wherein lead electrodes are placed in an atrial appendage 15. The lead electrodes stimulate RA 16 downstream of dysfunctional SA node 30 and the stimulating pulse travels on to AV node 32, bundle of His 40, and Purkinje fibers 46 to restore physiological contraction of the heart. However, if a patient has a dysfunctional AV node 32, pacing in atrial appendage 15 will not be effective, since it is upstream of a block caused by the damage.

Pacing at the bundle of His 40 provides the advantage of utilizing the normal conduction system of the heart to carry out ventricular depolarizations. In other words, stimulation provided at the bundle of His will propagate rapidly to the entire heart via the right bundle 42, the left bundle (not shown), and the Purkinje fibers. This provides synchronized and efficient ventricular contraction, which is not replicated when the pacing is performed from the apex of the right ventricle because the electrical activity propagates via slowly conducting myocardial tissue as opposed to the rapidly conducting Purkinje network.

Of other excitable tissue in the body, cardiac cells allow a controlled flow of ions across the membranes. This ion movement across the cell membrane results in changes in transmembrane potential, which is a trigger for cell contraction. The heart cells can be categorized into several cell types (e.g. atrial, ventricular, etc.) and each cell type has its own characteristic variation in membrane potential. For example, ventricular cells have a resting potential of ~−85 mV. In response to an incoming depolarization wave front, these cells fire an action potential with a peak value of ~20 mV and then begin to repolarize, which takes ~350 ms to complete. In contrast, SA nodal cells do not have a stable resting potential and instead begin to spontaneously depolarize when their membrane potential reaches ~−50 mV. Cells, such as SA nodal cells, that do not have a stable resting transmembrane potential, but instead increase spontaneously to the threshold value, causing regenerative, repetitive depolarization, are said to display automacity.

Cardiac muscle cells are structurally connected to each other via small pore-like structures known as gap junctions. When a few cardiac cells depolarize, they act as a current source to adjacent cells causing them to depolarize as well; and these cells in turn impose on further adjacent cells, and so on. Once depolarization begins within a mass of cardiac cells, it spreads rapidly by cell-to-cell conduction until the entire mass is depolarized causing a mass of cardiac cells to contract as a unit.

The cells in the SA node are specialized pacemaker cells and have the highest firing rate. Depolarization from these cells spreads across the atria. Since atrial muscle cells are not connected intimately with ventricular muscle cells, conduction does not spread directly to the ventricle. Instead, atrial depolarization enters the AV node, and after a brief delay, is passed on to the ventricles via the bundle of His and Purkinje network, initiating cellular depolarization along the endocardiuim. Depolarization then spreads by cell-to-cell conduction throughout the entire ventricular mass.

The SA node's unique cells include a combination of ion channels that endow it with its automacity. A review of the features of cardiac electrical function and description of the current understanding of the ionic and molecular basis, thereof, can be found in Schram et al., "Differential Distribution of Cardiac Ion Channel Expression as a Basis for Regional Specialization in Electrical Function," *Circ. Res.*, Vol. 90, pages 939-950 (2002), the teachings of which are herein incorporated by reference.

Some of the unique features of the SA node cells include the absence of Na$^+$ channels ($I_{Na}$) and inwardly rectifying K$^+$ ($I_{K1}$) channels. In the absence of sodium current, the upstroke of SA node action potential is primarily mediated by L-type Ca$^{2+}$ channels ($I_{CaL}$). SA node cells do not have a stable resting potential because of the lack of the $I_{K1}$ and begin to depolarize immediately after the repolarization phase is complete. The maximum diastolic potential for SA node cells is approximately −50 mV compared to −78 mV and −85 mV for atrial and ventricular cells, respectively. The slow depolarization phase is mediated by activation of "funny current" ($I_f$) and T-type Ca$^{2+}$ channels and deactivation of slow and rapid potassium ($I_{Ks}$, and $I_{Kr}$, respectively). The rate of pacemaker discharge in the SA node in a normally functioning heart is approximately in the range of about 60 to 100 beats per minute.

In a heart with dysfunctional SA node pacemaker function, the other structures of the heart with intrinsic pacemaking activity can take over the pacing function. However the increased heart rate is not sufficient to support normal circulation. A method of the present invention includes genetically modifying the cells of the cardiac conduction system, such as the Purkinje fibers to modify the electrophysiology and pacing rate to resemble more closely the electrophysiology and pacing rate of the specialized pacemaker cells of the SA node.

Figure 2:
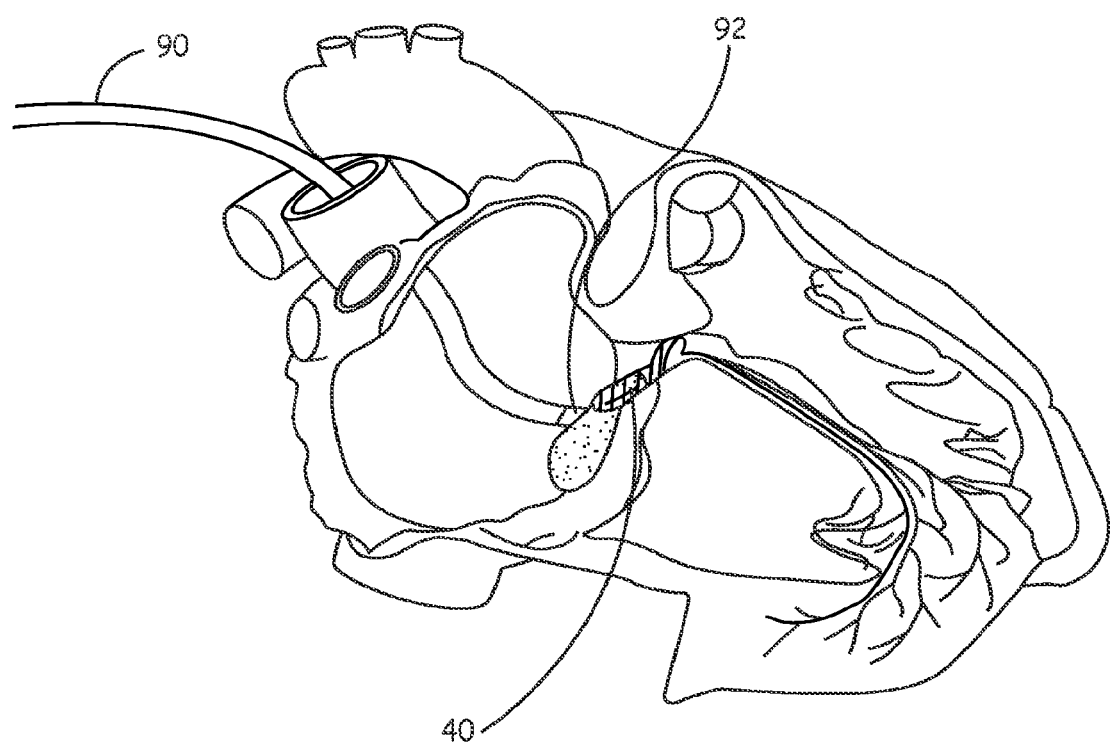
FIG. 2 is a schematic diagram of a right side of a heart, similar to FIG. 1, in which a guiding catheter is positioned for delivery of the genetic construct of the invention.

FIG. 2 is a schematic diagram of the right side of a heart similar to that shown in FIG. 1, wherein a guide catheter 90 is positioned for delivery of the genetic construct of the invention. A venous access site (not shown) for catheter 90 may be in a cephalic or subclavian vein and means used for venous access are well known in the art, including the Seldinger technique performed with a standard percutaneous introducer kit. Guide catheter 90 includes a lumen (not shown) extending from a proximal end (not shown) to a distal end 92 that slideably receives delivery system 80. Guide catheter 90 may have an outer diameter between approximately 0.115 inches and 0.170 inches and is of a construction well known in the art. Distal end 92 of guide catheter 80 may include an electrode (not shown) for mapping electrical activity in order to direct distal end 92 to an implant site near bundle of His 40. Alternatively, a separate mapping catheter may be used within lumen of guide catheter 90 to direct distal end 92 to an implant site near bundle of His 40, a method well known in the art.

In one embodiment, a sufficient amount of a bio-pacemaker composition that includes a genetic construct or vector is delivered to the cells of the conduction system, where the genetic construct modifies one or more properties of the conduction system to increase the intrinsic pacemaking rate of such cells. In an embodiment of the invention, the bio-pacemaker composition is delivered to Purkinje fiber cells and will: 1) increase the inward T-type $Ca^{2+}$ current, 2) decrease $Na^+$ current; or 3) increase funny current ($I_f$), or 4) increase the outward $K^+$ current.

The cells of the conduction system may be modified to maximize the transformation of these cells into the primary pacemaker and to increase their intrinsic pacing rate to a level resembling that of the SA node. Desirably, the intrinsic pacing rate of the modified cells is increased to a level substantially identical to that of the SA node. As used herein, "resembling" or "resembles" means that the pacing rate of the modified cells is increased to a level of at least about 85% of the pacing rate of the SA node cells for a particular patient when the heart is functioning normally and "substantially identical" means that the pacing rate of the modified cells is increased to a level of at least about 95% of the pacing rate of the SA node cells for the patient when the SA node of the heart is functioning normally.

The terms "encodes", "encoding", "coding sequence", and similar terms as used herein, refer to a nucleic acid sequence that is transcribed (in the case of DNA) and translated (in the case of mRNA) into a polypeptide in vitro or in vivo when place under control of the appropriate regulatory sequences. A number of genetic modifications may be carried out in accordance with the present invention. For example, the cells of the conduction system are genetically modified to increase the inward $Ca^{2+}$ current by delivering a bio-pacemaker composition to these cells. As a specific example, for the Purkinje fibers, the composition includes a coding sequence that encodes a T-type $Ca^{2+}$ channel resulting in the exogenous expression of T-type $Ca^{2+}$ channels. Exogenous expression of this channel will facilitate the depolarization characteristics of Purkinje fiber cells necessary to increase their intrinsic pacing rate.

In accordance with another embodiment of the invention, genetic modifications to increase $I_K$ are undertaken. Relative to the SA node, Purkinje fiber cells express low levels of the channels, $I_{Kr}$ or $I_{Ks}$ that are responsible for $I_K$. The $I_{Kr}$ channel is comprised of two subunits ($\alpha$ and $\beta$), encoded by erg1 and MiRP, respectively, that coassemble to produce functional channels. Heterologous expression of erg1 produces potassium currents similar to $I_{Kr}$. The $I_{Ks}$ channel is comprised of an $\alpha$ subunit encoded by KvLQT1 and an accessory $\beta$ subunit encoded by minK. Coassembly of both these subunits is necessary to elicit $I_{Ks}$.

In the SA node, deactivation of $I_{Kr}$ and $I_{Ks}$ during late phase repolarization facilitates depolarization at a rate sufficient to maintain an adequate heart rate. Weak $I_K$ in the cells of the Purkinje fibers increases action potential duration (APD). Extended APD implies that intrinsic pacemaking rate of the Purkinje cells is comparatively slow and insufficient to sustain normal circulation. The APD of Purkinje fiber cells can be shortened to more closely resemble the APD of the SA node by increasing $I_K$ with exogenous expression of $I_{Kr}$ and/or $I_{Ks}$. Delivering a bio-pacemaker composition including coding sequences for $I_{Kr}$ or $I_{Ks}$ to Purkinje fiber cell can increase exogenous expression of these channels. For exogenous expression of $I_{Kr}$, the composition may include the erg1 coding sequence or alternatively, both erg1 and MiRP coding sequences may be delivered to the cells. For exogenous expression of $I_{Ks}$, the bio-pacemaker composition includes the minK and KvLQT1 coding sequences.

According to another embodiment, a targeted region of the conduction system, for example, Purkinje fiber cells, can be modified to decrease sodium current ($I_{Na}$). In the SA node, L-type $Ca^{2+}$ channels mediate the upstroke of action potentials. However, the upstroke of action potentials in wild type Purkinje fiber cells is mediated by $I_{Na}$. Mediation by $I_{Na}$ results in a more rapid upstroke relative to that of the SA node. The upstroke of Purkinje fiber AP's can be slowed by suppression of endogenous $I_{Na}$. Endogenous $I_{Na}$ expression can be suppressed by introducing polynucleotide sequences or molecules that interfere with the expression of wild type of $I_{Na}$.

The pacing rate of any cardiac cell type is the product of the composition of channels expressed by the cell as well as electronic influences exerted by neighboring cells. For example, evidence suggests that the ventricles exert electronic influences on the Purkinje cells at the Purkinje-ventricular junction, thereby inhibiting its pacing rate. Thus, to be effective, proposed genetic modifications must take into account the wild type channel expression as well as influences exerted by neighboring cells.

The electronic influences of the ventricles can be decreased by electrically uncoupling the Purkinje fibers from ventricular cells. Since electrical impulse spread through the ventricles via gap junctions, uncoupling the gap junctions in the vicinity of the genetic modification can help to further enhance the effects of the modification by augmenting increase in pacing rate for a given amount of cellular modification. This is particularly useful where the genetic modifications are occurring in the more distal portions of the Purkinje fibers.

Gap junctions can be uncoupled by interfering with the formation of connexons. Ventricular gap junctions can be preferentially uncoupled while leaving the gap junctions of the Purkinje cells or other cells intact, by the targeted interference of connexin 43 (CX43), the predominant connexin protein of ventricular gap junctions. Accordingly, the present invention provides for the preferential uncoupling of ventricular gap junctions in the area of the Purkinje-ventricular junction, and more preferably in the immediate area of any of the preceding genetic modifications.

Any combination or all of the above-described genetic manipulations may be carried out. For example, the cells of the conduction system, for example, Purkinje cells, may be modified as to elicit exogenous expression of the T-type $Ca^{2+}$ channel. Alternatively, the cells of the conduction system (e.g. Purkinje fibers) are modified so that they express the T-type $Ca^{2+}$ channel, $I_f$, $I_{Kr}$ and $I_{Ks}$. In the SA node, all these channels contribute to the pacemaking rate, in some instances, it may, therefore, be desirable to modify all four characteristics of the Purkinje fibers simultaneously or sequentially. Alternatively, the cells may be modified so as to express one or more of the above-mentioned channels concurrently with suppression of endogenous $Na^+$.

Figure 3A:
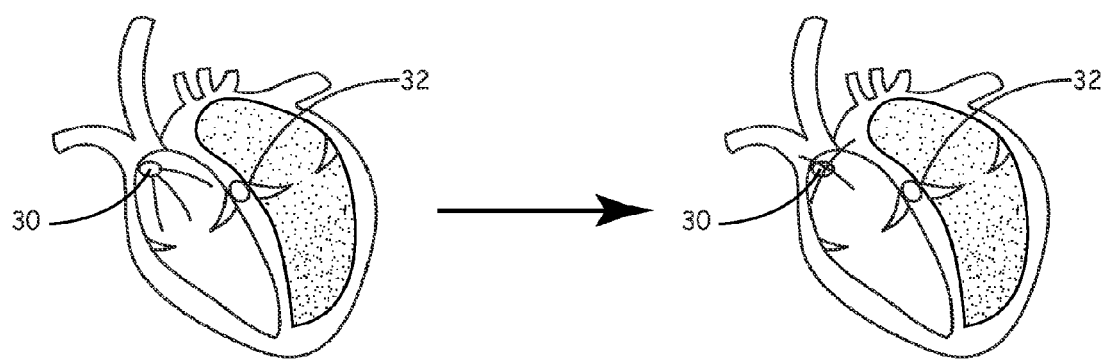
FIGS. 3A and 3B are schematics illustrating how an embodiment of the invention operates.
Figure 3B:
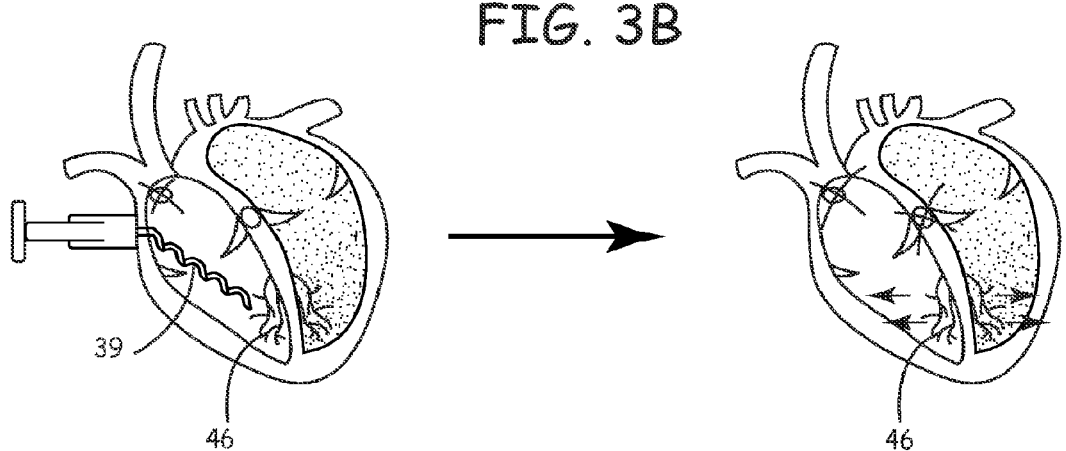

The schematics of FIGS. 3A and 3B illustrate the effect of the genetic modification of the invention. FIG. 3A illustrates a heart with the normal pacemaker function in the SA node 30 impaired. FIG. 3B illustrates the delivery of a bio-pacemaker composition comprising genetic vector or construct 39 to the Purkinje fiber cells 46 of the cardiac conduction system. After the genetic vector or construct has been delivered to the host cell and modified gene expression has occurred, at least a portion of the cells of the cardiac conduction system's electrophysiology will be altered to more closely resemble that of a normally functioning SA node. A bio-pacemaker composition may alternatively be delivered to the SA node 30, AV node 32 or to conduction system in the ventricles, which comprises of proximal bundle of His, intermediate left and right branches, and distal Purkinje network/fibers embedded intimately in the ventricular endocardium.

In situations where SA node and AV node are not amenable to genetic modification, upper regions of the conduction system in the ventricles, viz bundle of His or upper portions of left and right bundle branches would be most preferred site for bio-pacemaker formation. However, since these structures are small and sheathed with a layer of connective tissue, targeting them may be relatively difficult. In contrast, targeting the distal Purkinje fibers is easier because of their abundance and known localization on the endocardium. For a pacemaker in the distal purkinje fibers, although the activation sequence within the ventricular conduction system (i.e. His bundle, bundle branches and purkinje network) will be different from normal activation sequence, it will still result in synchronous ventricular contraction because conduction velocity within the conduction system is approximately an order faster (2-4 m/s in conduction system versus 0.3 to 1.0 m/s in the ventricular muscle) than the intermuscular conduction velocity.

FIGS. 4A and 4B illustrate the effect of genetic alteration on the pacing rate of the Purkinje fibers in the conduction system obtained with modification of electrophysiological characteristics. As shown in FIG. 4A, in the wild type Purkinje fiber cell, $I_{Na}$ mediates depolarization. However, as shown in FIG. 4B, after genetic modification using the method of the present invention relating to the delivery of one or more genetic constructs including a coding sequence capable of expressing the $I_{Kr}$ and $I_{Ks}$ channels, the T-type $Ca^{2+}$ channel, $I_f$ channel, as well as a polynucleotide sequence capable of suppressing $I_{Na}$, depolarization is mediated by both the L-type $Ca^{2+}$ and T-type $Ca^{2+}$ channels and the firing rate of the modified cardiac Purkinje fiber cells is increased to the level of the SA node.

Figure 5A:
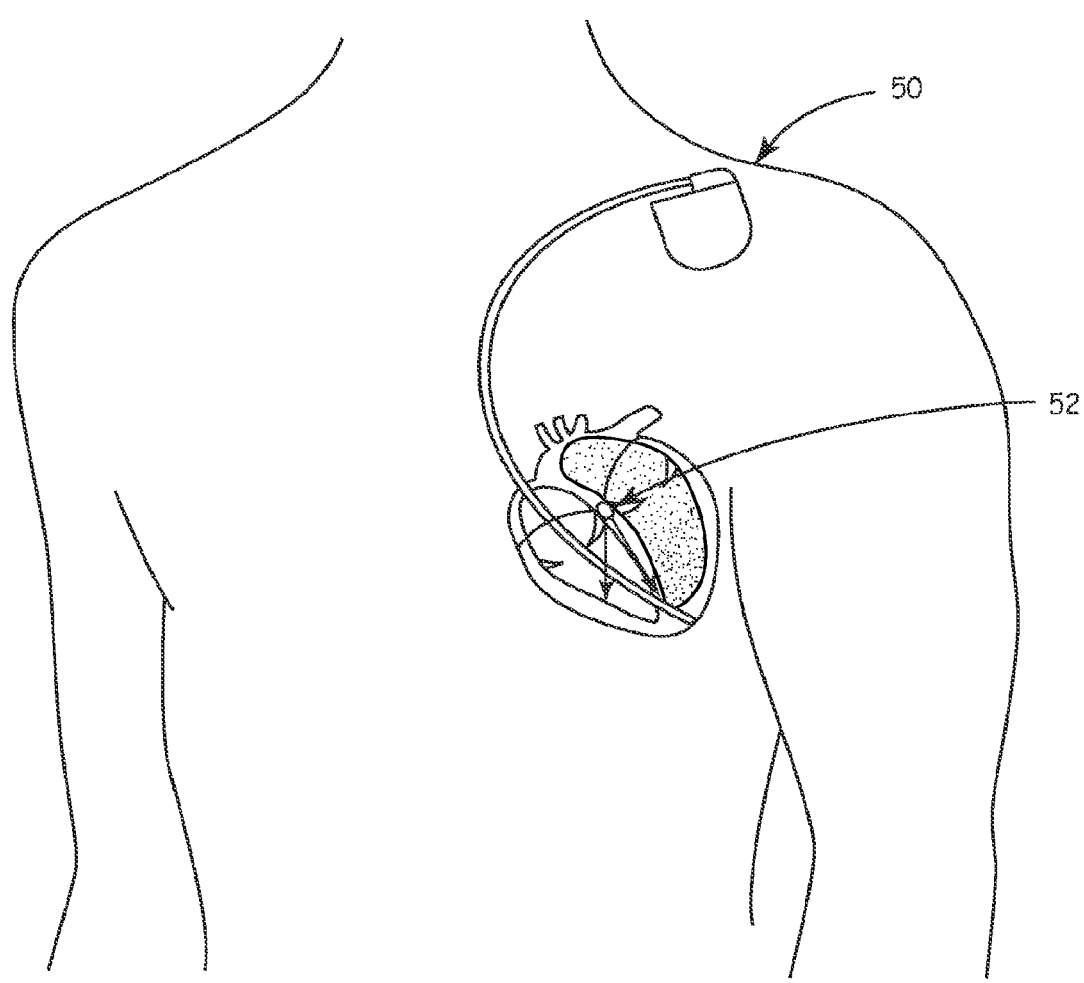
FIG. 5A illustrates the use of a small implantable backup pacemaker working in cooperation with the bio-pacemaker of the invention based on transforming the cells of the AV node in the conduction system.

Cardiac disease often onsets suddenly, and the patient may require immediate pacemaker treatment. As is well known, the effects of gene or polynucleotide transfer may not be appreciated for as long as several days. Thus, as depicted in FIG. 5A, an implantable pacemaker 50 is implemented with bio-pacemaker 52 of the invention to act as a bridge in the days following the genetic treatment of the present invention before full expression or suppression of channels or other proteins is accomplished. In this embodiment, an implantable pacemaker 50, is implanted consistent with methods well known in the art. The implantable pacemaker 50 may be adapted or programmed to serve several purposes. For example, the implantable pacemaker 50 may act as backup to the bio-pacemaker of the present invention. In the event the bio-pacemaker 52 fails, malfunctions, or a slowing in the pacing rate is sensed, implantable pacemaker 50 may be activated to take over the pacing function. Further, implantable pacemaker 50 may supplement the activity of the bio-pacemaker 52 in the event the bio-pacemaker 52 fails to produce sufficient stimulation. Other purposes for employing an implantable pacemaker to supplement or to be used with the genetic modification of the Purkinje fibers will be evident to a person of ordinary skill in the art.

Figure 5B:
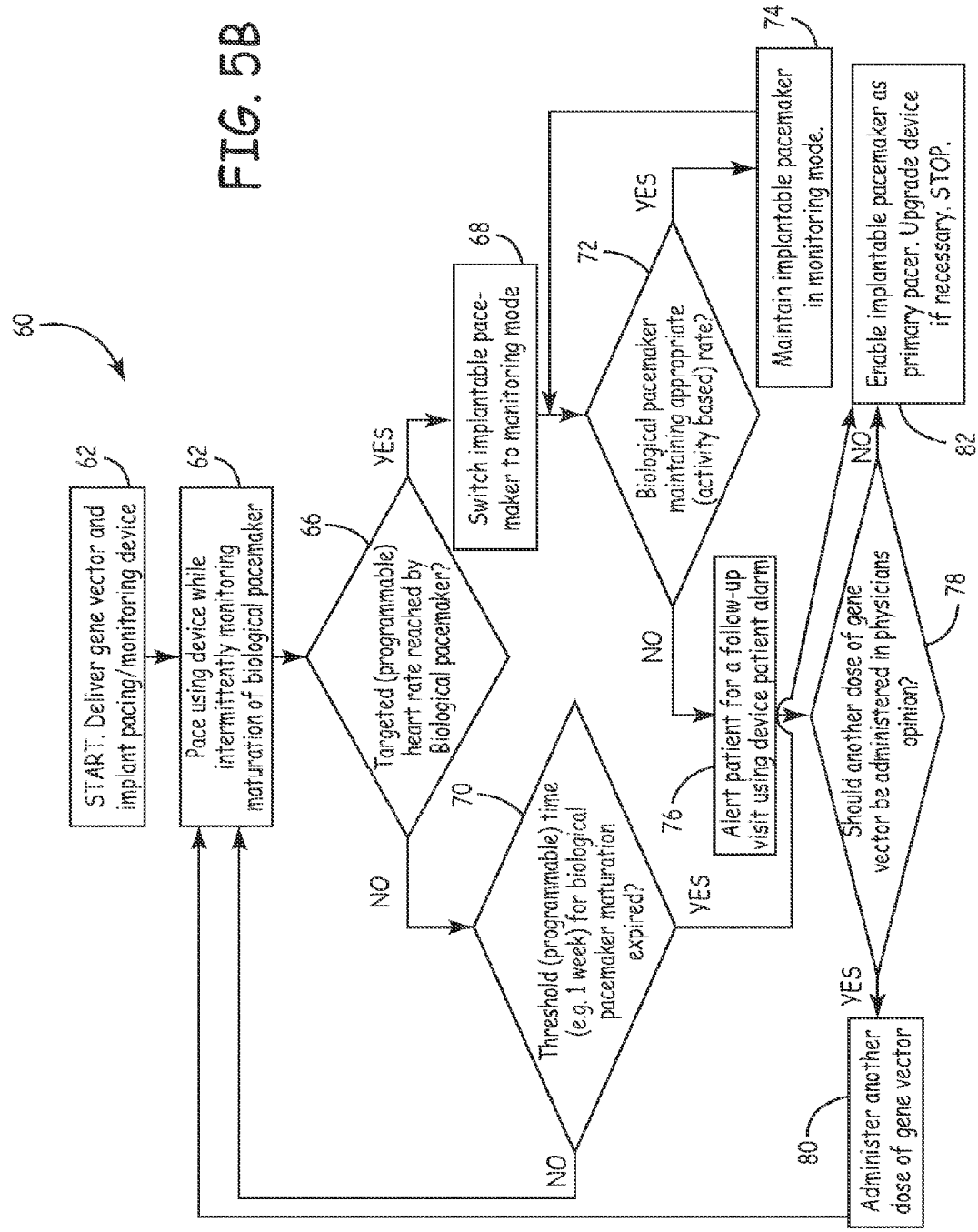
FIG. 5B is a logic flow diagram depicting the operational logic of the invention.

The cooperative operation of implantable pacemaker 50 and bio-pacemaker 52 is described in FIG. 5B. Specifically, one aspect of the operational logic between the implantable pacemaker 50 and the bio-pacemaker 52 is shown. Computer implemented software logic system 60 includes logic step 62 where a gene vector is delivered to a targeted region of the cardiac conduction system and a pacemaker is implanted under logic step 62. Under logic step 64, the pacemaker is used to pace the patient's heart while intermittently monitoring the maturation of the biological pacemaker or the number of therapy occasions at which the gene vector that has been delivered. Under decision step 66, when a targeted or programmable heart rate is reached by the biological pacemaker, the implantable medical device is switched to a monitoring mode under logic step 68. However, if the targeted heart rate has not been reached by the biological pacemaker, then under decision logic step 70, the time of the biological pacemaker maturation is checked whether it has expired. If the time has expired, then the logic proceeds to enable implantable pacemaker as a primary pacemaker under logic step 82. If, on the other hand, the threshold time for the biological pacemaker has not expired, the system reverts back to logic step 64 where pacing is done by the device while intermittently monitoring maturation of the biological pacemaker. Referring now to logic step 66, if the targeted heart rate is reached by the biological pacemaker, then under logic step 68, the implantable pacemaker is switched to only monitor the operation of the biological pacemaker. Subsequently, under logic step 72, the biological pacemaker is checked to see whether it is maintaining the appropriate rate. If the appropriate pacing rate is maintained by the biological pacemaker, the implantable pacemaker is maintained in a monitoring mode and in the alternative, if the biological pacemaker is not keeping the appropriate rate, a patient alert is triggered to make the patient aware for a follow-up visit. Typically, the alert is communicated via device patient alarm, or other equivalent perceptible means. Further, under logic step 78, the system looks to see whether another dose of gene vector should be administered based upon a physician's opinion. If such a dose is confirmed, another dose of gene vector under logic step 80 is administered and the logic reverts back to logic step 64 to pace using the device while intermittently monitoring the maturation of the biological pacemaker. In the alternate, if the administration of another dose of gene vector is not advisable, the system reverts to logic step 82 where it would enable the implantable pacemaker to operate as the primary pacer. Further, the implantable pacemaker may act as backup to the bio-pacemaker of the present invention. In the event the bio-pacemaker fails, malfunctions, or a slowing in the pacing rate is sensed, the implantable pacemaker may be activated to take over the pacing function. Specifically, the implantable pacemaker may supplement the activity of the bio-pacemaker in the event the bio-pacemaker fails to produce sufficient stimulation. Other purposes for employing an implantable pacemaker to supplement or to be used with the genetic modification of the AV node includes chronic data management for diagnostic purposes and tracking and monitoring long term performance of the genetic pacemaker.

Ablation of the upper region of the AV node may be carried out in conjunction with the genetic treatment and implantable pacemaker implantation. Ablation may be necessary to electrically uncouple the atria from the AV node in patients experiencing uncomfortable junctional beats and those suffering from atrial fibrillation.

Delivery of the bio-pacemaker composition comprising a genetic construct can be carried out according to any method known in the art. It is only necessary that the genetic construct reach a small portion of the cells that are targeted for gene manipulation (e.g. cells of the Purkinje fibers). The genetic construct may be injected directly into the myocardium as described by R. J. Guzman et al., *Circ. Res.*, 73:1202-1207 (1993). The delivery step may further include increasing microvascular permeability using routine procedures, including delivering at least one permeability agent prior to or during delivery of the genetic construct. Perfusion protocols useful with the methods of the invention are generally sufficient to deliver the genetic construct to at least about 10% of cardiac myocytes in the mammal. Infusion volumes from about 0.5 to about 500 ml are useful. Methods for targeting non-viral vector genetic constructs to solid organs, for example, the heart, have been developed such as those described in U.S. Pat. No. 6,376,471, the teachings of which are hereby incorporated by reference.

Therapeutic methods of the invention comprise delivery of an effective amount of a genetic construct of the invention to the cells of the conduction system, such as cardiac Purkinje fiber cells, to increase the intrinsic pacing rate of these cells to resemble the pacing rate of the SA node cells when functioning normally. The delivery or administration may be accomplished by injection, catheter and other delivering means known in the art. A delivery system for delivering genetic material in a targeted area of the heart is described in PCT Publication No. WO 98/02150, assigned to the assignee of the present application, the teachings of which are herein incorporated by reference.

The genetic construct can be delivered into a cell by, for example, transfection or transduction procedures. Transfection and transduction refer to the acquisition by a cell of new genetic material by incorporation of added nucleic acid molecules. Transfection can occur by physical or chemical methods. Many transfection techniques are known to those of ordinary skill in the art including, without limitation, calcium phosphate DNA co-precipitation, DEAE-dextrin DNA transfection, electroporation, naked plasmid adsorption, and cationic liposome-mediated transfection. Transduction refers to the process of transferring nucleic acid into a cell using a DNA or RNA virus. Suitable viral vectors for use as transducing agents include, but are not limited to, retroviral vectors, adeno associated viral vectors, vaccinia viruses, an Semliki Foret virus vectors.

In the context of the present invention, methods for detecting modulation of the cells of the conduction system of the heart by electrophysiological assay methods relates to any conventional test used to determine the cardiac action potential characteristics, such as action potential duration (APD). An example of such a method related to performing such tests is disclosed by Josephson M E, *Clinical Cardiac Electrophysiology: Techniques and Interpretations*, Lea & Febiger. (1993), pp 22:70, the teachings of which are herein incorporated by reference. Briefly, a standard electrophysiological assay includes the following steps: providing a mammalian heart (in vivo or ex vivo), delivering to the heart a genetic construct or modified cells of the invention, transferring the genetic construct and/or modified cells into the heart under conditions which can allow expression of an encoded amino acid sequence; and detecting increase of at least one electrical property in the cells of the heart to which the genetic construct and/or modified cells were delivered, wherein at least one property is the pacing rate of the cells, relative to a baseline value. Baseline values will vary with respect to the particular target region chosen in the conduction system. Additionally, modulation of cardiac electrical properties obtained with the methods of the invention may be observed by performing a conventional electrocardiogram (ECG) before and after administration of the genetic construct of the invention and inspecting the ECG results. ECG patterns from a heart's electrical excitation have been well studied. Various methods are known for analyzing ECG records to measure changes in the electrical potential in the heart associated with the spread of depolarization and repolarization through the heart muscle.

In the invention, a bio-pacemaker composition that includes a polynucleotide capable of increasing the expression of a particular ion channel or suppressing, in whole or in part, the expression or function of an ion channel may be made. Polynucleotides encoding the ion channel of choice can be made by traditional PCR-based amplification and known cloning techniques. Alternatively, a polynucleotide of the invention can be made by automated procedures that are well known in the art. A polynucleotide of the invention should include a start codon to initiate transcription and a stop codon to terminate translation.

Suitable polynucleotides for use with the invention can be obtained from a variety of public sources including, without limitation, GenBank (National Center for Biotechnology Information (NCBI)), EMBL data library, SWISS-PROT (University of Geneva, Switzerland), the PIR-International database; and the American Type Culture Collection (ATCC) (10801 University Boulevard, Manassas, Va. 20110-2209). See generally, Benson, D. A. et al, *Nucl. Acids. Res.*, 25:1 (1997) for a description of GenBank. The particular polynucleotides useful with the present invention are readily obtained by accessing public information from GenBank.

Any DNA vector or delivery vehicle can be utilized to transfer the desired nucleotide sequence to the cells of the cardiac Purkinje fibers. For example, $\alpha_{1H}$ cDNA, HCN1-HCN4, erg1, MinK, MiRP, KvLQT1 cDNA, or all may be cloned into a viral vector such as an adenoviral associated vector (AAV). Alternatively, other viral vectors such as, herpes vectors, and retroviral vectors such as lentiviral vectors may be employed. The type of viral vector selected is dependent on the target tissue and the length of the sequence to be delivered. For a discussion of viral vectors see *Gene Transfer and Expression Protocols*, Murray ed., pp. 109-206 (1991). Alternatively, non-viral delivery systems may be utilized. For example, liposome:DNA complexes, plasmid:liposome complexes, naked DNA, DNA-coated particles, or polymer based systems may be used to deliver the desired sequence to the cells. The above-mentioned delivery systems and protocols therefore can be found in *Gene Targeting Protocols*, Kmeic 2ed. pp. 1-35 (2002) and *Gene Transfer and Expression Protocols*, Vol. 7, Murray ed. pp 81-89 (1991).

AAV vectors can be constructed using techniques well known in the art. Typically, the vector is constructed so as to provide operatively linked components of control elements. For example, a typical vector includes a transcriptional initiation region, a nucleotide sequence of the protein to be expressed, and a transcriptional termination region. Typically, such an operatively linked construct will be flanked at its 5' and 3' regions with AAV ITR sequences, which are required viral cis elements. The control sequences can often be provided from promoters derived from viruses such as, polyoma, Adenovirus 2, cytomegalovirus, and Simian Virus 40. Viral regulatory sequences can be chosen to achieve a high level of expression in a variety of cells. Alternatively, ubiquitously expressing promoters, such as the early cytomegalovirus promoter can be utilized to accomplish expression in any cell type. A third alternative is the use of promoters that drive tissue specific expression. This approach is particularly useful where expression of the desired protein in non-target tissue may have deleterious effects. Thus, according to another preferred embodiment, the vector contains the proximal human brain natriuretic brain (hBNP) promoter that functions as a cardiac-specific promoter. For details on construction of such a vector see LaPointe et al., "Left Ventricular Targeting of Reporter Gene Expression In Vivo by Human BNP Promoter in an Adenoviral Vector," *Am. J. Physiol. Heart Circ. Physiol.*, 283:H1439-45 (2002).

Vectors may also contain cardiac enhancers to increase the expression of the transgene in the targeted regions of the cardiac conduction system. Such enhancer elements may include the cardiac specific enhancer elements derived from Csx/NRx2.5 regulatory regions disclosed in the published U.S. Patent Application 20020022259, the teachings of which are herein incorporated by reference.

Introducing the AAV vector into a suitable host, such as yeast, bacteria, or mammalian cells, using methods well known in the art, can produce AAV viral particles carrying the sequence of choice.

A number of different constructs can be generated in accordance with the invention. For example, a construct can be produced that includes the coding sequence of the $\alpha_{1H}$ subunit of the T-type $Ca^{2+}$ channel, the $\alpha$ and/or $\beta$ subunit of $I_{Kr}$, or the $\alpha$ and/or $\beta$ subunits of $I_{Ks}$. Constructs containing the coding sequence of one of the channels or subunit thereof are referred to as single gene constructs. These constructs are useful when practicing embodiments that call for the introduction of only one channel sequence or when it is desired to titrate the expression of the transgenes relative to each other. Such differential expression of the channels can be accomplished by generating vectors with varied promoters or administration of differing dosages. Alternatively, multiple transgenes can be co-delivered by compound vectors as is known by those skilled in the art.

Targeted gene suppression can be accomplished by a number of techniques. In general, polynucleotides that interfere with expression of $I_{Na}$ or CX43 at the transcriptional or translational level may be administered to cells of the Purkinje fibers. For example, a polynucleotide that either encodes for a dominant negative form of the $I_{Na}$ channel or CX43, functions as a decoy, or sterically blocks transcription by triplex formation may be employed. Alternatively, antisense approaches may be utilized. Furthermore, coassembly of functional CX42 subunits with Cx43 subunits to form heteromeric gap junction channels may also aid in lowering gap junctional conductance.

Dominant negative gene suppression is achieved by introducing mutations into the wildtype gene and expressing the mutated gene in a cell expressing wild type protein. The dominant negative protein acts to decrease level of a particular protein by interfering with the assembly or function of the wild type protein. The mutations in the wild type gene may be introduced by site-directed mutagenesis.

Effective dominant negative mutations of the $I_{Na}$ channel or CX43 may include those directed to residues that are important for the trafficking of the protein to the cell surface or folding of the wild type protein and thereby decrease the number of functional protein at the cell surface or at the gap junction. Additional dominant negative mutations include the introduction of hydrophilic amino acids in hydrophobic transmembrane regions. Such alterations prevent the effective assembly of the channel into the cell membrane. Preferably, the dominant negative is specific to targeted gene so that the function of other proteins is not altered. Furthermore, in the case of ion channels, mutations should be designed so as to not alter ionic specificity of the channel.

A particular construct for use in the present invention is an CX43 construct with the A253V mutation. This mutation has been shown to effectively suppress CX43. See Omori et al., "Role of Connexin (gap junction) Genes in Cell Growth Control: Approach with Site-Directed Mutagensis and Dominant Negative Effects," *Tox. Lett.*, Aug., p. 105-110 (1998). A vector including the A253V CX43 gene may be introduced into the cells of the Purkinje fibers by techniques already described.

A construct useful for the dominant negative suppression of $I_{Na}$ is SCN5A R1432G. The replacement of arginine with glycine at position 1432 interferes with trafficking of the channel to the plasma membrane. Baroudi et al., "Novel Mechanism for Brugada Syndrome," *Circ Res.*, 88:e78-e83 (2001). Decreased levels of the channel at the cell surface will decrease $I_{Na}$.

Suppression of $I_{Na}$ and/or CX43 in the cells of the cardiac conduction system through a method of this invention can also be accomplished by the administration of oligonucleotides that act as a decoy for transcription factors for the relevant gene. Decoys function to suppress the expression of a gene by competing with native regulatory sequences. The oligonucleotide should be specific for transcription factors that regulate the relevant genes. The oligonucleotide may be administered to the cells of the Purkinje fibers by techniques well known in the art.

The invention may also be practiced employing triple helix technology to suppress $I_{Na}$ and/or CX43 expression. Thus, a single strand oligonucleotide may be introduced to the cells of the targeted region of the cardiac conduction system (e.g. Purkinje fibers). Suppression of a targeted gene is accomplished by inhibition of transcription via the formation of a triple helix structure comprised of the targeted double strand DNA sequence and the oligonucleotide. Potential triple helix sites may be identified using computer software to search targeted gene sequence with a minimum of 80% purine over a 15 basepair stretch. The oligonucleotide may be synthesized with 3' propanolamine to protect against 3' exonucleases present in cells. For a discussion of triple helix techniques see Vasquez et al. Triplex-directed site-specific genome modification. *Gene Targeting Protocols*, Kmiec 2ed. pp. 183-200 (2000).

In accordance with the invention, $I_{Na}$ and/or CX43 expression may also be suppressed using antisense techniques. Antisense therapeutics is based on the ability of an antisense sequence to bind to mRNA and block translation. Antisense oligonucleotides must have high specificity for the target gene to avoid disruption of non-targeted gene expression. Artificial antisense oligodeoxyribonucleotides are favored because they can be synthesized easily, are readily transferred to the cytoplasm of cardiac conduction system cells using liposomes, and resist nuclease activity.

Constructs of the present invention can be targeted to cells of the Purkinje network by methods known to those skilled in the art. Advantage can be taken of the expression of cell surface receptors unique to specific cells. For example, one such receptor, preferentially expressed on the surface of Purkinje cells, is the cysteinyl leukotriene 2 receptor ($CysLT_2$). This receptor distinguishes Purkinje cells from neighboring cells such as ventricular cells and can be utilized to target constructs of the invention preferentially to Purkinje cells. However, it is to be understood that in the practice of the present invention, any receptor specific to Purkinje cells may be utilized for specific targeting.

Targeted delivery requires the modification of vehicle delivering the construct. Several methods for modification of viral vectors are possible. For example, viral protein capsids or proteins of the viral envelope may be biotinylated for subsequent coupling to a biotinylated antibody directed against a specific receptor or ligand therefore via a strepavidin bridge.

Alternatively, the viral delivery vehicle may be genetically modified so that it expresses a protein ligand for a specific receptor. The gene for the ligand is introduced within the coding sequence of a viral surface protein by for example, insertional mutagenesis, such that a fusion protein including the ligand is expressed on the surface of the virus. For details on this technique see Han et al., "Ligand-Directed Retroviral Targeting of Human Breast Cancer Cells," *Proc. Natl. Acad. Sci.*, 92:9747-9751 (1995). Viral delivery vehicles may also be genetically modified to express fusion proteins displaying, at a minimum, the antigen-binding site of an antibody directed against the target receptor. See e.g., Jiang et al., "Cell-Type-Specific Gene Transfer into Human Cells with Retroviral Vectors That Display Single-Chain Antibodies," *J. Virol.*, 72: 10148-10156 (1998).

Construct delivery vehicles may also be targeted to specific cells types utilizing bispecific antibodies produced by the fusion of anti-viral antibody with anti-target cell antibody. For details on this technique see Haisma et al., "Targeting of Adenoviral Vectors Through a Bispecific Single-Chain Antibody," *Cancer Gene Ther.*, 7:901-904 (2000) and Watkins et al., "The 'Adenobody' Approach to Viral Targeting: Specific and Enhanced Adenoviral Gene Delivery," *Gene Ther.*, 4:1004-1012 (1997).

Targeted construct delivery provides numerous advantages including increased transduction efficiency and the avoidance of genetic modification of cells in which the modification would have deleterious effects on the patient. Any technique for targeted gene therapy may be employed to target the construct of the invention to Purkinje cells.

As will be appreciated by those skilled in the art, the genetic manipulations described here may be practiced on stem cells without departing from the scope of the invention. The genetically modified stem cells can then be administered to the cells of the cardiac conduction system to elicit pacemaking activity. For example, cardiac myocardial cells derived from stem cells may be treated with the genetic procedures described herein and implanted into a region of the conduction system (e.g. Purkinje fiber) with a catheter or by direct injection to Purkinje fiber tissue.

The invention will be further described with reference to the following non-limiting Examples. It will be apparent to those skilled in the art that many changes can be made in the embodiments described in the Examples without departing from the scope of the present invention. Thus, the scope of the present invention should not be limited to the embodiments described in this application, but only by the embodiments described by the language of the claims and the equivalents of those embodiments.

EXAMPLE 1

Increased Intrinsic Pacemaking Rate of Genetically Modified Purkinje Fibers

Construction of rAAV Cloning Plasmids
Construct Generation

Figure 6:
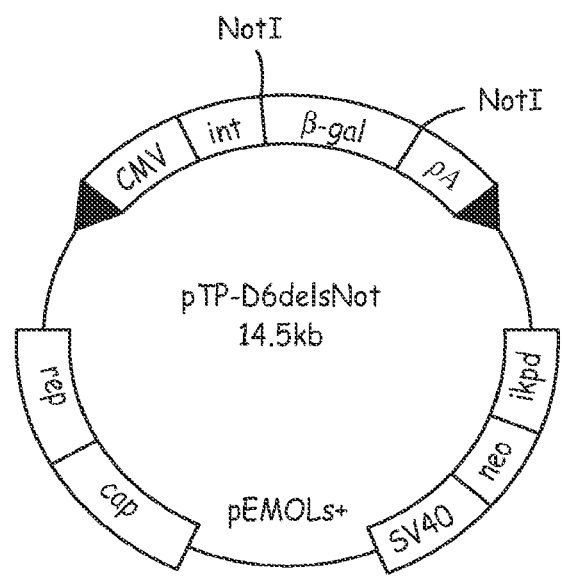
FIG. 6 is a schematic of the tripartite rAAV producer plasmid, pTP-D6deltaNot.

Genetic constructs useful in the bio-pacemaker composition of the invention can be generated using traditional techniques as described Schnepp and Clark in *Gene Therapy Protocol*, Morgan 2ed. pp. 490-510 (2002). Certain constructs of the present invention are generated by cloning the cDNA of minK (sequence listed in U.S. Pat. No. 6,323,026), KvLQT1 (GenBank accession No. AJ006345), erg (GenBank Accession No. AB009057), or α1H (GenBank Accession No. AF051946) into the rAAV producer plasmid, pTP-D6deltaNot. This tripartite plasmid, shown in FIG. 6, includes AAV rep and cap genes, a neomycin resistance gene flanked by the SV40 promoter and thymidine kinase polyadenylation signal, and a gene expression cassette flanked by AAV inverted terminal repeats (ITRs) and comprising the CMV promoter, SV40 large T-antigen intron, and polyadenylation signal, and beta galactocidase gene flanked by two unique NotI restriction sites. The cDNA for the channel of choice replaces the beta galactocidase gene by excising the gene using NotI restriction enzymes and cloning in the cDNA for the transgene. The resulting producer plasmid is used to produce rAAV particles. Alternatively, other constructs can be generated substituting alternative promoters. For example, a rAAV producer plasmid containing alternate promoters may be utilized.

The producer plasmid containing the transgene sequence is amplified by transformation of DH5-alpha *E. coli* and producing colonies screened by neomycin resistance. Producer plasmid is then isolated from resistant colonies and co-transfected with wild type adenovirus 5 (E1 deleted) into suitable host cells such as HeLA (for a discussion of the use of HeLA cells to produce rAAV particles see Clark et al., "Cell Lines for the Production of Recombinant Adeno-Associated Virus," *Human. Gene Ther.* 6:1329-1341 (1995). Host cells containing the vector are purified using ammonium sulfate followed by double cesium banding. The bands containing the viral particle are isolated from the cesium chloride preparation and dialysis into a Tris buffer, or other suitable buffer.

Generation of Dominant Negative Constructs

Dominant negative constructs are generated by synthesizing oligonucleotides comprising the gene coding sequence, including the dominant negative mutation using the site-directed mutagenesis system available in the Altered Sites® II Systems (Promega, Madison Wis.). This oligonucleotide is used as a primer to produce a plasmid containing the hybrid gene sequence. *E. coli* are transformed with the hybrid plasmid for amplification of the mutagenic gene. The mutant sequence is excised from the hybrid plasmid and cloned into the cloning plasmid as described above.

Suppressing the expression of CX43 using the dominant negative A253V is one way to modify Purkinje cells. The dominant negative sequence is produced by synthesizing a synthetic oligonucleotide including the A253V substitution as described above. The wild type sequence is deposited at GenBank accession No. AF151980.

Suppression of endogenous $I_{Na}$ is accomplished by delivery of a construct including the coding sequence of SCN5A including the R1432G mutation. The wild type sequence for SCNA5 is deposited at GenBank accession No. NM00035. The dominant negative sequence and construct is generated as described above.

Generation of $CysLT_2$ Specific Recombinant Vectors

Recombinant vectors are targeted to Purkinje cells that preferentially express the $CysLT_2$ receptor in their surface by modifying the viral protein capsid to contain an antibody directed against this receptor. Modified rAAV is produced by covalently linking anti-$CysLT_2$ polyclonal antibody (Caymen Chemical Company, Ann Arbor Mich.) to rAAV protein capsid via a biotin-strepavidin bridge.

To produce biotinylated rAAV, rAAV particles are concentrated to $3 \times 10^9$ to $5 \times 10^{10}$ and incubated on ice with 100-1000 ug/mL of photoactivatable biotin (Pierce Chemical Company, Rockford Ill.) in HBS buffer containing 5 mM Hepes, pH 7.3 and 150 mM NaCl. Following incubation, the incubate is irradiated at a wavelength of 350 nm for 5 minutes. Unbound biotin is removed on a Sephadex G-25M column (Sigma Aldrich, St. Louis, Mo.) equilibrated with HBS.

Polyclonal anti-$CysLT_2$ antibodies (Caymen Chemical Company, Ann Arbor, Mich.) are concentrated to 2 mg/mL in 0.1M $NaHCO_3$, pH 8.4. Biotin-X-NHS (Calbiochem, San Diego, Calif.). DMSO (Aldrich, St. Louis, Mo.) is added to the antibody for a concentration of 80 ug of biotin per mg of antibody. The biotin and antibody are allowed to incubate at room temperature for 30 minutes. Unbound biotin is removed on a Sephadex G-25M column (Sigma Aldrich, St. Louis, Mo.) and the buffer replaced with PBS.

The biotinylated antibody and biotinylated rAAV are incubated in 500 ug/mL neutravidin (Pierce Chemical Company Rockford, Ill.) for 30 minutes at room temperature to produce rAAV presenting the anti-$CysLT_2$ on their protein capsids. Excess avidin is removed by separation on a Sephacryl 300 column (Sigma-Aldrich, St. Louis, Mo.).

In vivo Vector Administration

Adult guinea pigs are infected by intermuscular injection (via catheter) of a solution of saline with a viral concentration range of approximately $3\times10^{10}$ to $3\times10^{14}$ plaque forming units (PFU). For targeted injection to the right side of the heart, the Purkinje fibers are accessed via the superior vena cava or femoral veins, the catheter is then guided to the right atrium, through the tricupsid valve, and to the right ventricle. The left side of the heart can be targeted in a similar fashion. The left atrium is accessed from the right atrium via the septum primum. From the left atrium, the catheter is guided through the bicuspid valve to the left ventricle.

All patents and publications referenced herein are hereby incorporated by reference in their entireties. It will be understood that certain of the above-described structures, functions and operations of the above-described preferred embodiments are not necessary to practice the present invention and are included in the description simply for completeness of an exemplary embodiment or embodiments. In addition, it will be understood that specific structures, functions and operations set forth in the above-referenced patents can be practiced in conjunction with the present invention, but they are not essential to its practice. It is therefore to be understood that within the scope of the appended claims, the invention may be practiced otherwise than as specifically described without actually departing from the spirit and scope of the present invention.

What is claimed is:

1. A kit comprising an implantable pacemaker and a bio-pacemaker composition comprising at least two coding sequences selected from the group consisting of: (i) a coding sequence that encodes, in myocardial cells of cardiac Purkinje fibers, at least one T-type $Ca^{2+}$ channel subunit, wherein at least one of the T-type $Ca^{2+}$ channel subunits is $\alpha_{1H}$; (ii) a coding sequence that encodes, in myocardial cells of cardiac Purkinje fibers, one or more molecules that increase $I_f$, wherein at least one of the one or more molecules that increase $I_f$ is selected from the group consisting of HCN1, HCN2, HCN3, or HCN4; and (iii) a coding sequence that encodes, in myocardial cells of cardiac Purkinje fibers, one or more molecules that increases $I_K$, wherein at least one of the one or more molecular that increases $I_K$ is selected from the group consisting of erg1, MiRP, MinK, or KvLQT1.

2. The kit of claim 1, wherein the bio-pacemaker composition further comprises a coding sequence that encodes a molecule or molecules that suppress the expression of wild type sodium channels producing sodium current.

3. The kit of claim 2, wherein the coding sequence encodes a dominant-negative form of the wild type sodium channel.

4. The kit of claim 1, further comprising a coding sequence that encodes one or more molecules that electrically uncouple cells of the Purkinje fibers from ventricular cells.

5. The kit of claim 4, wherein the coding sequence encodes connexin 42 or connexin 43.

6. The kit of claim 1, wherein the implantable pacemaker is configured to pace the heart if the intrinsic pacing rate of the heart is less than a predetermined level.

* * * * *